United States Patent [19]

Grosselin et al.

[11] Patent Number: 4,906,795
[45] Date of Patent: Mar. 6, 1990

[54] PROCESS FOR THE PREPARATION OF VITAMIN A

[75] Inventors: Jean-Michel Grosselin; Claude Mercier, both of Lyon, France

[73] Assignee: Rhone-Poulenc Sante, Antony, France

[21] Appl. No.: 277,199

[22] Filed: Nov. 29, 1988

[30] Foreign Application Priority Data

Dec. 1, 1987 [FR] France ............................... 87 16629

[51] Int. Cl.$^4$ ............................................. C07C 35/18
[52] U.S. Cl. ..................................... 568/824; 568/862; 568/856
[58] Field of Search ......................... 568/824, 862, 880

[56] References Cited

U.S. PATENT DOCUMENTS

| 2,834,813 | 5/1958 | Oroshnil | 568/824 |
| 2,839,585 | 6/1958 | Hawks | 568/824 |
| 3,210,427 | 10/1965 | Redel et al. | 568/824 |
| 3,499,044 | 3/1970 | Stugis | 568/824 |
| 4,268,454 | 5/1981 | Pez et al. | 568/880 |
| 4,321,414 | 3/1982 | Costa | 568/862 |
| 4,623,750 | 11/1986 | Schulte-Elte et al. | 568/824 |

FOREIGN PATENT DOCUMENTS

| 2032906 | 1/1971 | Fed. Rep. of Germany | 568/824 |
| 2412517 | 10/1974 | Fed. Rep. of Germany | 568/824 |

Primary Examiner—Werren B. Lone
Attorney, Agent, or Firm—Stevens, Davis, Miller & Mosher

[57] ABSTRACT

Vitamin A containing practically no 2-cis or 6-cis isomer is prepared by hydrogenation of the aldehyde of vitamin A, optionally in the form of a complex with hydroquinone, in the presence of a ruthenium hydride catalyst.

11 Claims, No Drawings

PROCESS FOR THE PREPARATION OF VITAMIN A

The present invention relates to the preparation of vitamin A by the reduction of the corresponding aldehyde.

Vitamin A [3,7-dimethyl-9-(2,6,6-trimethyl-1-cyclohexenyl)-2,4,6,8-nonatetraen-1-ol] or retinol and the aldehyde of vitamin A (retinal or retinene) exhibit maximum biological activity when they are in the 2,6-trans,trans form.

The aldehyde of vitamin A in the 2,6-trans,trans form can be separated from the other isomers by the formation of a complex with hydroquinone (U.S. Pat. No. 2,683,746).

Vitamin A can be obtained by reduction of the aldehyde of vitamin A, if appropriate in the form of a complex with hydroquinone. However, reduction of the aldehyde group is often accompanied by isomerization of the double bonds in the 2-position and 6-position.

According to U.S. Pat. No. 2,839,585 and T. Mukaiyama and A. Ishida, Chem. Letters, 1975, p. 1201, the complex of the aldehyde of all-trans-vitamin A with hydroquinone is reduced to all-trans-vitamin A, in good yield, by using sodium borohydride in methanol.

It is also known to prepare vitamin A by the catalytic hydrogenation of retinene. According to French patent 2,234,258, the reduction can be carried out in the presence of a catalyst based on platinum and cobalt, in an aliphatic alcohol. However, this process, which requires the use of a substantial amount of platinum, yields a vitamin A in which the ratio 2-cis/all-trans is of the order of 1/7.

USSR Patent 1,141,170 proposes carrying out the reduction in the presence of a complex catalyst $Ir/Co/BaO/\gamma\text{-}Al_2O_3$. However, although this process gives very good yields with a single all-trans stereoisomerism, it requires the use of an iridium-based catalyst which is expensive and has a low productivity.

According to G. Mestroni et al., "Homogeneous Catalytic Reduction of Carbonyl, Azomethine and Nitro Groups" in "Aspects of Homogeneous Catalysis" by R. Ugo, 1981, vol. 4, p. 74, published by D. Reidel (Holland), it is known to hydrogenate linear, branched or aromatic aldehydes in the presence of the complex $RuCl_2(CO)_2[P(C_6H_5)_3]_2$ under conditions which, especially in the case of linear aldehydes, frequently lead to secondary reactions. According to W. Strohmeier and K. Holke, J. Organometal. Chem., 193, C63–C66 (1980), the selective hydrogenation of $\alpha,\beta$-unsaturated aldehydes to unsaturated alcohols is preferably carried out using the ruthenium complex $RuCl_2(CO)_2[P(C_6H_{11})_3]_2$, while ruthenium hydrides, [e.g. $RuH_2[P(C_6H_5)_3]_4$] give unsatisfactory results.

It has now been found that the hydrogenation of all-trans-retinal, if appropriate in the form of a complex with hydroquinone, to all-trans-retinol can be carried out selectively, with no secondary isomerization reaction, by using a ruthenium hydride catalyst, which may be generated in situ, if necessary in the presence of a base or a buffer medium for neutralizing the acidity of the medium.

The ruthenium hydrides are preferably associated with a ligand (L) which contains phosphorus (phosphines, phosphites), oxygen (acetate, trifluoroacetate), nitrogen (hydroxypyridines), sulphur or silicon.

The catalysts used for carrying out the process of the invention can be well-defined, previously made compounds, e.g. $RuH_2(PPh_3)_4$, or they can be generated in situ from precursors such as $Ru(C_8H_8)_2(PPh_3)_2$ or $RuCl_2(PPh_3)_4$.

Of especial interest are the ruthenium hydrides $RuH_2(PPh_3)_4$, $RuH(OAc)(PPh_3)_4$ and $RuH(2\text{-hydroxypyridine})(PPh_3)_3$. $RuH_2(PPh_3)_4$ can be prepared under the conditions described by R. O. Harris et al, J. Organometal. Chem., 54, 259–264 (1973). $RuH(OAc)(PPh_3)_4$ can be prepared according to the method described in Inorg. Synthesis, 16, p. 53 and 75 to 79, or in Comprehensive Organometallic Chemistry, Vol. IV, Chapter 32.3.2., p. 717. $RuH_2(PPh_3)_3$ can be generated in situ, by the method described by G. Wilkinson et al, J. Chem. Soc. Dalton, 1739 (1978), from $Ru(C_8H_8)_2(PPh_3)_3$, or by the method described in J. Organometal. Chem., 142, C55–C57 (1977), from $RuCl_2(PPh_3)_4$. The hydrogenation is generally carried out at a temperature of between 0° and 100° C., preferably of between 20° and 50° C., in an organic solvent. It is particularly advantageous to carry out the reaction under a pressure of between 1 and 200 bar and preferably of between 1 and 20 bar. The reduction is generally complete after a reaction time of one hour.

The polar organic solvent used is preferably an alcohol (methanol, ethanol, isopropanol), which is optionally associated with a non-polar solvent selected from aliphatic hydrocarbons (pentane, hexane, heptane, octane), alicyclic hydrocarbons (cyclohexane) and aromatic hydrocarbons (benzene, toluene, xylene), an ether (diethyl ether, diisopropyl ether, tetrahydrofuran, dioxane) or an ester (methyl acetate, ethyl acetate, butyl acetate).

It is particularly advantageous to add to the polar solvent, or solvent mixture, an amount of water which can be up to 10% of the total volume of solvent, in order to prevent the acetal formation in particular.

In general, from 0.1 to 0.0001 mol, preferably from 0.03 to 0.003 mol, of the catalyst is used per mol of retinal.

The following Examples illustrate the invention.

EXAMPLE 1

$RuH_2[P(C_6H_5)_3]_4$ (708 mg; 0.61 mmol) and then the complex of the aldehyde of vitamin A with hydroquinone (RHQ complex) (2.303 g, i.e. 6.4 mmol of retinal) are introduced into a 250 cc reactor at 25° C. under an argon atmosphere. (The RHQ complex has a titre of 79.6% and contains 96.1% of all-trans isomer, 3.5% of 2-cis isomer and 0.4% of 6-cis isomer, as well as 1.1% of iodine and 252 ppm of sulphur.) With the exclusion of light, the mixture is dissolved in isopropanol (100 cc) containing water (2 cc). The reactor is purged with hydrogen under a pressure of 1 bar for 15 minutes. The reaction mixture is then stirred at 1000 rpm. The reaction is followed by the volume of hydrogen absorbed and by high performance liquid chromatography [Si60 Lichrosorb 125×4 column—Hexane/ethyl acetate (90/10 by volume)—Absorption at 325 nm—Flow rate: 1 cc/minute].

After 1 hour, the volume of hydrogen absorbed is 155 cc (theory: 154 cc).

High performance liquid chromatography (HPLC) shows that:

the degree of conversion of the retinal is greater than or equal to 99%, and the isomeric distribution of the retinol obtained is as follows:

| all-trans-retinol | 96.2% |
|---|---|
| 2-cis-retinol | 3.3% |
| 6-cis-retinol | 0.5% |

The yield is of the order of 94%.

EXAMPLE 2

RuH$_2$[P(C$_6$H$_5$)$_3$]$_4$ (67 mg; 0.058 mmol) and RHQ complex (2.302 g) are introduced into a 125 cc Hastelloy C autoclave. The autoclave is purged and isopropanol (50 cc) containing water (1 cc) is then introduced. A hydrogen pressure of 20 bar is established and stirring is then started at a temperature of the order of 20° C. Stirring is continued for 40 minutes, i.e. until the absorption of hydrogen is complete. After degassing, HPLC analysis of the homogeneous light brown liquid obtained shows that:

the degree of conversion of the retinal is greater than or equal to 99.9%, and the isomeric distribution of the retinol obtained is as follows:

| all-trans-retinol | 96.0% |
|---|---|
| 2-cis-retinol | 3.6% |
| 6-cis-retinol | 0.4% |

The yield is of the order of 94%.

EXAMPLE 3 (Comparative Example)

The reaction is carried out under the conditions of Example 13 of French patent 2 234 258 using a pre-reduced catalyst PtO$_2$/Co(OAc)$_2$.4H$_2$O and the same RHQ complex as in Example 1.

After a reaction time of 40 minutes under a pressure of 1 bar at 25° C., HPLC analysis shows that:

the degree of conversion of the retinal is of the order of 78%, and the isomeric distribution of the retinol obtained is as follows:

| all-trans-retinol | 82% |
|---|---|
| 2-cis-retinol | 11.8% |
| 6-cis retinol | 6.2% |

The yield is of the order of 52%.

EXAMPLE 4

RuH(OAc)[P(C$_6$H$_5$)$_3$]$_4$ (53 mg) and RHQ complex (4.6361 g) are introduced into a 125 cc Hastelloy C autoclave. The autoclave is purged and methanol (50 cc) and water (1 cc) are then added. A hydrogen pressure of 20 bar is established and the mixture is then stirred for 3 hours 45 minutes at a temperature of the order of 20° C. After degassing, HPLC analysis of the homogeneous light brown liquid obtained shows that:

the degree of conversion of the retinal is of the order of 99.5%, and the isomeric distribution of the retinol obtained is as follows:

| all-trans-retinol | 96.2% |
|---|---|
| 2-cis-retinol | 3.3% |
| 6-cis-retinol | 0.5% |

The yield is of the order of 92.5%.

EXAMPLE 5

RuH$_2$[P(C$_6$H$_5$)$_3$]$_4$ (59.3 mg) and RHQ complex (4.6250 g) are introduced into a 125 cc Hastelloy C autoclave. The autoclave is purged and methanol (50 cc) and water (1 cc) are then introduced. A hydrogen pressure of 20 bar is established. The autoclave is placed in an oven preheated to 50° C. and the mixture is then stirred for 20 minutes. After cooling and degassing, HPLC analysis of the light brown liquid obtained shows that:

the degree of conversion of the retinal is greater than 99.9%, and the isomeric distribution of the retinol obtained is as follows:

| all-trans-retinol | 97.4% |
|---|---|
| 2-cis-retinol | 2.1% |
| 6-cis-retinol | 0.5% |

The yield is of the order of 96%.

EXAMPLE 6

RuH$_2$[P(C$_6$H$_5$)$_3$]$_3$ (59.4 mg) and RHQ complex (4.6198 g) containing the aldehyde of all-trans-vitamin A (12.34 mmol) are introduced into a 125 cc Hastelloy C autoclave. The autoclave is purged and methanol (50 cc) and water (1 cc) are then introduced. A hydrogen pressure of 20 bar is established at a temperature of the order of 20° C. The mixture is stirred for 1 hour 10 minutes. After degassing, HPLC analysis of the homogeneous light brown liquid obtained shows that:

the degree of conversion of the retinal is of the order of 99.9%, and the isomeric distribution of the retinol obtained is as follows:

| all-trans-retinol | 95.8% |
|---|---|
| 2-cis-retinol | 3.8% |
| 6-cis-retinol | 0.4% |

The yield is of the order of 97%.

EXAMPLE 7

The procedure is the same as in Example 6 except that retinal (0.893 g) containing 95% of all-trans isomer and RuH$_2$[P(C$_6$H$_5$)$_3$]$_3$ (21.1 mg) dissolved in methanol (20 cc) and water (0.4 cc) are used. A hydrogen pressure of 50 bar is established at 50° C. The mixture is stirred for 2 hours 10 minutes. After degassing, HPLC analysis of the liquid obtained shows that:

the degree of conversion of the retinal is of the order of 100%, and the isomeric distribution of the retinol obtained is as follows:

| all-trans-retinol | 96% |
|---|---|
| 2-cis-retinol | 2.5% |
| 6-cis-retinol | 0.45% |

The yield of all-trans-retinol is of the order of 85%.

EXAMPLE 8

The procedure is the same as in Example 5 except that 95% ethanol is used as the solvent. Hydrogenation is carried out under a pressure of 20 bar at 50° C. for 20 minutes. After degassing, HPLC analysis of the liquid obtained shows that:

the degree of conversion of the retinal is 98%, and
the isomeric distribution of the retinol obtained is as follows:

| | |
|---|---|
| all-trans-retinol | 95.8% |
| 2-cis-retinol | 3.1% |
| 6-cis-retinol | 0.4% |

The yield of all-trans-retinol is 92.8%.

EXAMPLE 9

The procedure is the same as in Example 5 except that RuH(2-hydroxypyridine)(PPh$_3$)$_3$ (59 mg) and RHQ complex (4.62 g) are used. The autoclave is purged and 95% ethanol (50 cc) is then introduced. A hydrogen pressure of 20 bar is established at a temperature of the order of 50° C. and the mixture is then stirred for 30 minutes. After cooling and degassing, HPLC analysis of the homogeneous brown liquid obtained shows that:

the degree of conversion of the retinal is 37%, and
the all-trans-retinol represents 90.5% of the mixture of retinols.

The yield of all-trans-retinol is of the order of 35%.

EXAMPLE 10 (Comparative Example)

RuCl$_2$[P(C$_6$H$_5$)$_3$]$_4$ (72.8 mg) and RHQ complex (2.3050 g) are introduced into a 125 cc Hastelloy C autoclave. The autoclave is purged and isopropanol (50 cc) and water (1 cc) are then added. A hydrogen pressure of 20 bar is established at a temperature of the order of 20° C. and the mixture is then stirred for 3 hours. After degassing, a light brown liquid is obtained which quickly turns dark red. HPLC analysis of the liquid obtained shows that:

the degree of conversion of the retinal is 46%, and
the isomeric distribution of the retinol obtained is as follows:

| | |
|---|---|
| all-trans-retinol | 71.5% |
| 2-cis-retinol | 28.5% |

The yield of all-trans-retinol is of the order of 5%.

We claim:

1. A process for the preparation of vitamin A containing practically no 2-cis or 6-cis isomer which comprises reducing retinal with hydrogen in a polar organic solvent selected from the group consisting of alcohols of 1 to 3 carbon atoms, and mixtures of an alcohol of 1 to 3 carbon atoms with an aliphatic, alicyclic or aromatic hydrocarbon, an ether or an ester, in the presence of a catalyst selected from the group consisting of ruthenium hydrides and ruthenium hydrides associated with a ligand containing phosphorus, oxygen, nitrogen, sulphur or silicon.

2. Process according to claim 1, wherein the solvent also includes up to 10% of the total volume of the solvent of water.

3. Process according to claim 1, wherein the reduction is carried out under a hydrogen pressure of between 1 and 200 bar.

4. Process according to claim 3, wherein the reduction is carried out under a hydrogen pressure of between 1 and 20 bar.

5. Process according to claim 1, wherein the reduction is carried out at a temperature of between 0° and 100° C.

6. Process according to claim 5, wherein the reduction is carried out at a temperature of between 20° and 50° C.

7. Process according to claim 1, wherein from 0.1 to 0.0001 mol of catalyst is used per mol of retinal.

8. Process according to claim 7, wherein from 0.03 to 0.003 mol of catalyst is used per mol of retinal.

9. Process according to claim 1, wherein the catalyst is RuH$_2$(PPh$_3$)$_4$, RuH(OAc)(PPh$_3$)$_4$, or RuH(2-hydroxypyridine)(PPh$_3$)$_3$.

10. Process according to claim 1 wherein retinal in the form of its complex with hydroquinone is reduced.

11. Process according to claim 1, wherein the said catalyst is a ruthenium hydride associated with a phosphine, phosphite, acetate, trifluoroacetate or hydroxypyridine ligand.

* * * * *